United States Patent [19]

Abramowitz et al.

[11] Patent Number: 5,158,777
[45] Date of Patent: Oct. 27, 1992

[54] CAPTOPRIL FORMULATION PROVIDING INCREASED DURATION OF ACTIVITY

[75] Inventors: Robert Abramowitz, Somerset; Yatinda M. Joshi, Piscataway; Nemichand B. Jain, Monmouth Junction, all of N.J.

[73] Assignee: E. R. Squibb & Sons, Inc., Princeton, N.J.

[21] Appl. No.: 745,656

[22] Filed: Aug. 16, 1991

Related U.S. Application Data

[63] Continuation-in-part of Ser. No. 480,987, Feb. 16, 1990, abandoned.

[51] Int. Cl.$^5$ .................... A61K 31/195; A61K 9/24; A61K 9/26; A61K 9/56
[52] U.S. Cl. ................................. 424/458; 424/461; 424/462; 424/469; 424/471; 424/480; 424/482; 424/494; 424/495; 424/497; 518/929
[58] Field of Search ............... 424/425, 451, 456, 469, 424/482, 495, 497, 499; 518/824, 906, 929, 960, 963, 964, 965

[56] References Cited

U.S. PATENT DOCUMENTS

| | | | |
|---|---|---|---|
| 4,105,776 | 8/1978 | Ondetti et al. | 424/274 |
| 4,309,404 | 1/1982 | DeNeale et al. | 424/21 |
| 4,666,705 | 5/1987 | De Crosta et al. | 424/482 |
| 4,728,512 | 3/1988 | Mehta et al. | 424/458 |
| 4,756,911 | 7/1988 | Drost et al. | 424/468 |
| 4,794,001 | 12/1988 | Mehta et al. | 424/458 |
| 4,800,084 | 1/1989 | Zerbe | 424/458 |
| 4,808,413 | 2/1989 | Joshi et al. | 424/458 |
| 4,814,178 | 3/1989 | Bolton et al. | 424/467 |
| 4,814,179 | 3/1989 | Bolton et al. | 424/467 |
| 4,851,228 | 7/1989 | Zentner et al. | 424/456 |
| 4,910,021 | 3/1990 | Davis et al. | 424/456 |

OTHER PUBLICATIONS

Translation Japanese Patent Application No. 61-36217.
Physicians Desk Reference, 44th Edition, pp. 2129-2135.
FMC, "Preparation Of Avicel Spheres Using Several Methods of Manufacture", 1985.
Rohm Pharma, "Eudragit L and S".
Morflex, "Citrate Esters As Plasticizers For Aqueous Based Pharmaceutical Coatings".
Kodak, "Eastman HPMCP Enteric Coating Material (Hydroxypropyl Methylcellulose Phthalate)".
Kodak, "Eastman Cellulose Acetate Trimellitate (GA-T) Enteric Coating Material".
Kodak, "Eastman C-A-P Enteric Coating Material".
Hu et al., "Passive and Carrier-Medicated..." Jour. of Pharmaceutical Sciences, vol. 77, 1007-1011 (1988).

*Primary Examiner*—Thurman K. Page
*Assistant Examiner*—E. J. Webman
*Attorney, Agent, or Firm*—Stephen B. Davis

[57] ABSTRACT

A formulation comprising captopril within an enteric or delayed release coated pH stable core combined with additional captopril that is available for immediate release following administration.

7 Claims, No Drawings

CAPTOPRIL FORMULATION PROVIDING INCREASED DURATION OF ACTIVITY

RELATED APPLICATION

This application is a continuation-in-part of Ser. No. 480,987 filed Feb. 16, 1990.

BACKGROUND OF THE INVENTION

Captopril, 1-[(2S)-3-mercapto-2-methyl-1-oxopropyl]-L-proline, is an angiotensin converting enzyme inhibitor approved for use as an antihypertensive agent for the treatment of congestive heart failure. Other indications are currently being evaluated.

Captopril is available in the United States from E. R. Squibb & Sons, Inc., in a tablet form in amounts of 12.5 mg., 25 mg., 50 mg., and 100 mg. of active ingredient. In addition, the combination of captopril and hydrochlorothiazide is available in the United States from E. R. Squibb & Sons, Inc. in tablets containing 25 mg. of captopril and 15 mg. or 25 mg. of hydrochlorothiazide and tablets containing 50 mg. of captopril and 15 or 25 mg. of hydrochlorothiazide.

In addition, captopril is available in Japan from Sankyo in a capsule containing an oil formulation of captopril which includes a fatty acid and ascorbic acid.

Joshi et al. in U.S. Pat. No. 4,808,413 disclose a controlled release formulation in the form of beadlets of a medicament such as captopril. The beadlets are formed of the medicament, a non-lipophilic binder-excipient, and an organic carboxylic acid such as citric acid at from at least 5%, preferably at least 10%, by weight of the formulation. The beadlets may also optionally include one or more auxilliary binders, one or more fillers or excipients, one or more lubricants, water, and/or other conventional additives.

Drost et al. in U.S. Pat. No. 4,756,911 disclose a controlled release formulation in the form of a coated tablet containing a core portion from which medicament is slowly released. The core includes hydroxypropylmethyl cellulose having a particular methoxyl content and viscosity as the primary gelling agent. Suitable medicaments are disclosed as including angiotensin converting enzyme inhibitors such as captopril.

Mehta et al. in U.S. Pat. Nos. 4,728,512 and 4,794,001 disclose formulations providing three distinct releases of medicament. The formulation consists of three groups of spheroids containing an active medicinal substance. The first group of spheroids is uncoated and rapidly disintegrates upon ingestion to release an initial dose of medicinal substance a second group of spheroids is coated with a pH sensitive coat to provide a second dose and a third group of spheroids is coated with a pH independent coat to provide a third dose. A powder blend of active medicinal substance may be substituted for the first group of uncoated spheroids. The therapeutic preparation may be utilized as a mixture of groups of spheroids in a capsule.

SUMMARY OF THE INVENTION

This invention is directed to captopril formulations having an increased duration of activity. The formulations include captopril in a pH stabilized core having an enteric or delayed release coating which protects the captopril until release in the colon. The coated pH stabilized core can be in the form of beads or core tablets. This coated core is then combined with additional captopril to give the final compositions which have a given amount of captopril available for immediate release following oral administration and an additional amount of pH stabilized captopril available for release in the colon.

The pH stabilized core in addition to containing captopril also includes one or more chelating agents, one or more antioxidants, and one or more binding agents. Other optional ingredients can be included within the core such as fillers, plasticizers, lubricants, as well as additional active ingredients such as a diuretic. The core is coated with an enteric coating which is selected to release the core contents when exposed to the lower part of the intestine or a delayed release coating which is selected to slowly release the core contents throughout the gastrointestinal tract.

DETAILED DESCRIPTION OF THE INVENTION

Captopril has been shown to be poorly absorbed in the colon (Hu et al., Journal of Pharmaceutical Sciences, Vol. 77, p. 1007-1011, 1988). It is believed that this is because captopril at the pH of the colon which varies from about 5 to 7.5 is converted into metabolites such as the disulfide and mixed disulfides. Thus, a captopril formulation in which at least a portion of the captopril is available in a pH stabilized form upon release into the colon will result in improved bioavailability and longer duration of activity.

This invention is directed to formulations for oral administration having a portion of the captopril in a pH stabilized core. The core can be in the form of beads or a tablet. The core is coated with an enteric or delayed release coating. This coated core is then compressed into tablets along with a powder mixture containing additional captopril or is then overcoated with a solution containing additional captopril or is then filled along with uncoated captopril beads into a capsule shell. As a result, the final compositions of this invention provide an amount of captopril for immediate release following oral administration and an additional amount of captopril in a pH stabilized environment available for release upon passage of the contents of the core through the digestive system into the colon.

The captopril formulations of this invention contain from about 12.5 mg. to about 100 mg. of total weight of captopril. The amount of captopril in the pH stabilized core will range from about 25% to about 75% by weight of the total captopril content, i.e., from about 3 mg. to about 75 mg., and will be present at from about 5% to about 50% by weight of the core. The core in addition to the captopril contains one or more chelating agents, one or more antioxidants, and one or more binders as well as other optional ingredients.

Suitable chelating agents for inclusion within the core include disodium edetate, capric and caprylic acid, the sodium salts of capric and caprylic acid, bile salts, and surfactants such as polysorbate 80. The chelating agent is included within the core at from about 1% to about 20% by weight of the core. The preferred chelating agent is disodium edetate.

Suitable antioxidants for inclusion within the core include ascorbic acid, erythorbic acid, and sodium erythorbate alone or in combination with a buffering agent such as sodium ascorbate. The anti-oxidant alone or with buffering agent are included at from about 10% to about 70% by weight of the core. The preferred antioxidant is ascorbic acid plus sodium ascorbate.

The core also includes one or more binding agents at from about 5% to about 30% by weight of the core. A suitable binder is microcrystalline cellulose which also functions as a spheronizing aid when the core is formulated as beads. Other suitable binders include povidone, gelatin, carbopol, sodium carboxymethylcellullose and cornstarch.

The enteric coating composition is formed from polymeric materials known to be insoluble below pH of 5. Suitable materials include methacrylic acid copolymers such as Eudragit L and S available from Rohm Pharma, hydroxypropyl methylcellulose phthalate such as HPMCP available from Eastman Kodak, and cellulose acetates such as cellulose acetate trimellitate available from Eastman Kodak as C-A-T, cellulose acetate phthalate available from Eastman Kodak as C-A-P, and blends of cellulose acetate trimellitate and cellulose acetate phthalate. The delayed release coating composition is formed from polymeric materials known to be water-insoluble but permeable to water and dissolved drugs. Suitable materials include ethylcellulose available as a dispersion from FMC and methacrylic acid copolymers such as Eudragit RS and RL available from Rohm Pharma. The enteric or delayed release coating composition can also include a plasticizer such as acetyltri-n-butyl citrate, triethyl citrate, acetyltriethyl citrate, tri-n-butyl citrate, castor oil, polyethylene glycol, or dibutyl phthalate. Talc or other glidants such as microfine silicas or metallic stearates can also be included in the enteric or delayed release coating composition.

The enteric or delayed release coated pH stabilized core in bead form can be prepared by any known sheronization techniques including the use of an extrusion/spheronization system, the use of a highshear mixer/granulator, the use of a rotating pan, the use of rotary fluidized-bed granulation, and the use of an agglomerator/powder applicator. For example, if the extrusion/spheronization system is employed, the beads would be prepared by mixing the captopril, chelating agent, antioxidant, binder, and any other optional ingredients in a planetary or high shear mixer for several minutes. Water is then added at from about 10% to 40% by weight of the mixture and granulation is continued. The granulated mass is then extruded through a screen. The extrudate is then processed in a spheronizer at a rotational speed of about 600 to 1000 rpm for about one to five minutes. The resulting spheres are dried and then coated with a solvent solution or dispersion of the enteric or delayed release polymeric coating composition in a fluidized-bed coater. The resulting enteric or delayed release coated pH stabilized core beads are then dried at 25° to 75° C. in either an oven-tray drier or a fluidized-bed drier.

The resulting pH stabilized enteric or delayed release coated beads can then be combined with captopril beads prepared without the coating step and filled into capsule shells.

Alternatively, the pH stabilized enteric or delayed release coated beads can be compressed into tablets with a powder mixture of captopril. The powder mixture in addition to the captopril can include a binder such as microcrystalline cellulose, a disintegrant such as cornstarch or croscarmellose, a lubricant such as stearic acid or magnesium stearate, and a glidant such as talc, microcrystalline cellulose, or magnesium stearate.

The pH stabilized core can also be prepared as a tablet which is then enteric or delayed release coated and finally overcoated with a coating solution containing additional captopril. The core tablet can be prepared by mixing the captopril, chelating agent, antioxidant and binder along with optional ingredients such as a lubricant, disintegrant, and glidant. Suitable lubricants include stearic acid and magnesium stearate, suitable disintegrants include cornstarch, and suitable glidants include talc. The resulting mixture is then compressed in a tablet forming press. This tablet is then coated with a solvent solution or dispersion of the enteric or delayed release polymeric coating composition and overcoated with a solution of captopril and a water soluble polymer. Suitable water soluble polymers include cellulose derivatives such as hydroxypropylcellulose, hydroxypropylmethyl cellulose, and blends thereof. A plasticizer such as polyethylene glycol, i.e., polyethylene glycol 3350 or 8000, can also be included in the outer coating.

An additional active ingredient particularly a diuretic such as hydrochlorothiazide can be included within the pH stabilized enteric or delayed release coated core or within the additional captopril powder, beads or coating or within both.

Coloring agents can be included within the enteric or delayed release coating or outer captopril overcoating.

The following examples are illustrative of the invention and exemplify preferred embodiments.

EXAMPLE 1

Enteric and delayed release coated pH stabilized core beads are prepared from the following ingredients:

| Composition of the beads | |
| --- | --- |
| Captopril | 60 mg. |
| Disodium edetate | 45 mg. |
| Ascorbic acid | 330 mg. |
| Sodium ascorbate | 24 mg. |
| Avicel ® RC 581 | 65 mg. |
| (contains 11% by weight of sodium carboxymethylcellulose and 89% by weight of microcrystalline cellulose) | |
| Composition of the enteric or delayed release coating | |
| Methacrylic acid copolymer* | 120 mg. |
| Acetyltri-n-butyl citrate | 30 mg. |
| Talc | 30 mg. |
| Composition of powder mixture | |
| Captopril | 40 mg. |
| Microcrystalline cellulose | 150 mg. |
| Cornstarch | 10 mg. |
| Stearic acid | 6 mg. |

*By employing Eudragit L from Rohm Pharma an enteric coating is obtained and by employing Eudragit RS from Rohm Pharma a delayed release coating is obtained.

The above core ingredients are mixed for 5 minutes in a planetary mixer (Hobart Co.) at about 60 rpm. A sufficient amount of purified water is added to the mixing powder in the same planetary mixer and granulated until a wet mass of suitable consistency is obtained. This granulated mass is passed through an extruder equipped with a 1.0 mm. screen. The extrudate is then processed in a spheronizer (Caleva, Model 15) at a rotational speed of about 850 rpm for two minutes.

The resulting spheres are transferred to a fluidized bed coater/drier, dried at 60° C. and then coated with a solution of the above enteric coating composition in acetone/isopropyl alcohol (6:4). The resulting coated spheres are then dried in a fluidized bed at 50° C. for 15 minutes.

The above powder mixture is prepared by blending the captopril, microcrystalline cellulose, and cornstarch in a Hobart mixer for 10 minutes. The coated beads are blended with the powder mixture for 5 minutes, the stearic acid is then added, and mixing is continued for an additional 5 minutes. This mixture is then compressed into tablets in a conventional rotary press.

EXAMPLE 2

Enteric or delayed release coated and uncoated core beads are prepared from the following ingredients:

| Composition of the beads to be coated | |
|---|---|
| Captopril | 50 mg. |
| Disodium edetate | 45 mg. |
| Ascorbic acid | 121 mg. |
| Sodium ascorbate | 9 mg. |
| Avicel ® RC 581 | 60 mg. |
| Composition of the enteric or delayed release coating | |
| Methacrylic acid copolymer* | 60 mg. |
| Acetyltri-n-butyl citrate | 15 mg. |
| Talc | 15 mg. |
| Composition of uncoated core beads | |
| Captopril | 50 mg. |
| Lactose | 37 mg. |
| Microcrystalline cellulose | 80 mg. |
| Citric acid | 18 mg. |

*See explanation in Example 1.

The uncoated beads and the enteric or delayed release coated core beads of above ingredients are prepared according to the procedure of Example 1.

A mixture of the coated and uncoated core beads is filled into a gelatin capsule shell.

EXAMPLE 3

A pH stabilized core tablet having an interior coating and an outer captopril containing overcoating is prepared from the following ingredients:

| Composition of the core tablets | |
|---|---|
| Captopril | 25 mg. |
| Disodium edetate | 22 mg. |
| Ascorbic acid | 125 mg. |
| Sodium ascorbate | 18 mg. |
| Microcrystalline cellulose | 50 mg. |
| Stearic acid | 3 mg. |
| Cornstarch | 20 mg. |
| Composition of interior coating | |
| Methacrylic acid copolymer* | 40 mg. |
| Acetyltri-n-butyl citrate | 10 mg. |
| Talc | 10 mg. |
| Composition of overcoat | |
| Captopril | 25 mg. |
| Hydroxypropylcellulose | 15 mg. |

*See explanation in Example 1.

The pH stabilized core tablet is prepared by mixing the above ingredients in a planetary mixer for 5 minutes and then compressing in a tablet press. The resulting core tablet is then coated with the above enteric or delayed release coating composition in acetone/isopropyl alcohol (6:4).

The enteric or delayed release coated core tablet is then overcoated with the above captopril composition in methanol and dried at 40° C.

What is claimed is:

1. A composition for oral administration of captopril consisting essentially of enteric or delayed release coated captopril containing pH stable beads combined with additional captopril for immediate release following administration, the pH stable core of each of said enteric or delayed release coated pH stable beads consisting essentially of on a weight percent basis from about 5% to about 50% captopril, from about 1% to about 20% of disodium edetate, from about 10% to about 70% of the combination of ascorbic acid and sodium ascorbate, and from about 10% to about 30% of the combination of microcrystalline cellulose and sodium carboxymethylcellulose, and the enteric or delayed release coating consisting essentially of a polymeric material selected from the group consisting of methacrylic acid copolymers, ethylcellulose, hydroxypropyl methylcellulose phthalate, cellulose acetate trimellitate, cellulose acetate phthalate, and blends of cellulose acetate trimellitate and cellulose acetate phthalate, a plasticizer selected from the group consisting of acetyltri-n-butyl citrate, triethyl citrate, acetyltriethyl citrate, tri-n-butyl citrate, castor oil, polyethylene glycol, and dibutyl phthalate, and a glidant selected from the group consisting of talc, microfine silicas, and metallic stearates.

2. The composition of claim 1 wherein said enteric or delayed release coated pH stable beads are combined with a powder mixture comprising captopril and an agent selected from the group consisting essentially ob binders, disintegrants, lubricants, glidants and mixtures thereof and said combination is compressed into a tablet.

3. The composition of claim 2 wherein said pH stable core consists essentially of captopril, disodium edetate, ascorbic acid, sodium ascorbate, sodium carboxymethylcellulose and microcrystalline cellulose, said enteric or delayed release coating consists essentially of methacrylic acid copolymer, acetyltri-n-butyl citrate, and talc, and said powder mixture consists essentially of captopril, microcrystalline cellulose, cornstarch, and stearic acid.

4. The composition of claim 1 wherein enteric or delayed release coated captopril containing beads are combined with uncoated captopril containing beads and said combination is filled into a capsule.

5. The composition of claim 4 wherein said pH stable core consists essentially of captopril, disodium edetate, ascorbic acid, sodium ascorbate, sodium carboxymethylcellulose and microcrystalline cellulose and said enteric or delayed release coating consists essentially of methacrylic acid copolymer, acetyltri-n-butyl citrate, and talc, and said uncoated core beads consist essentially of captopril, lactose, citric acid, and microcrystalline cellulose.

6. A tablet for oral administration of captopril consisting essentially of a pH stable core, an enteric or delayed release first coating, and a captopril containing second coating, said pH stable core consisting essentially of on a weight percentage basis from about 5% to about 50% captopril, from about 1% to about 20% of disodium edetate, from about 10% to about 70% of the combination of ascorbic acid and sodium ascorbate, and from about 10% to about 30% of the combination of microcrystalline cellulose, stearic acid, and cornstarch, said enteric or delayed release first coating consisting essentially of a polymeric material selected from the group consisting of methacrylic acid copolymers, ethylcellulose, hydroxypropyl methylcellulose phthalate, cellulose acetate trimellitate, cellulose acetate phthalate, and blends of cellulose acetate trimellitate and cellulose acetate phthalate, a plasticizer selected from the group consisting of acetyltri-n-butyl citrate, triethyl citrate, acetyltriethyl citrate, tri-n-butyl citrate, castor oil, polyethylene glycol, and dibutyl phthalate, and a glidant selected from the group consisting of talc, microfine silicas and metallic stearates, and said second coating consisting essentially of captopril and a water soluble polymer selected from the group consisting of hydroxypropylmethyl cellulose, hydroxypropylcellulose, and blends of hydroxypropylmethyl cellulose and hydroxypropylcellulose 7. The tablet of claim 6 wherein said pH stable core consists essentially of captopril, disodium edetate, ascorbic acid, sodium ascorbate, microcrystalline cellulose, stearic acid, and cornstarch, said enteric or delayed release first coating consists essentially of methacrylic acid copolymer, acetyltri-n-butyl citrate, and talc, and said second coating consists essentially of captopril and hydroxypropylcellulose.

* * * * *